United States Patent [19]

McAleer et al.

[11] 4,204,989
[45] May 27, 1980

[54] ISOLATION OF HEPATITIS B e ANTIGEN

[75] Inventors: William J. McAleer, Ambler; Edward H. Wasmuth, Telford, both of Pa.

[73] Assignee: Merck & Co., Inc., Rahway, N.J.

[21] Appl. No.: 968,896

[22] Filed: Dec. 13, 1978

[51] Int. Cl.$^2$ .............................................. C07G 7/00
[52] U.S. Cl. ........................... 260/112 B; 260/112 R; 424/85; 424/88
[58] Field of Search ...................... 260/112 B, 112 R; 424/85, 88

[56] References Cited

U.S. PATENT DOCUMENTS

| | | | |
|---|---|---|---|
| 3,636,191 | 1/1972 | Blumberg et al. | 424/89 |
| 3,838,144 | 9/1974 | Leach | 260/112 R |
| 3,887,697 | 6/1975 | Vyas et al. | 260/112 B X |
| 3,992,517 | 11/1976 | Lowke et al. | 260/112 R X |
| 3,994,870 | 11/1976 | Neurath et al. | 260/112 R |
| 4,024,243 | 5/1977 | McAleer et al. | 260/112 B X |
| 4,087,519 | 5/1978 | Trepo | 260/112 B X |

OTHER PUBLICATIONS

J. of Virology, vol. 7, No. 5, pp. 569–576 (Gerin et al.), 1971.
Science, 170, 332–333 (1970), Vyas et al.
Intervirology, 7:356–359 (1976), Neurath et al.

*Primary Examiner*—Howard E. Schain
*Attorney, Agent, or Firm*—Donald J. Perrella; Julian S. Levitt

[57] ABSTRACT

Hepatitis B e antigen or hepatitis B e antibody are separated from human biological fluid by centrifugation in a density gradient and isolated in the 1.04–1.15 g/cc density region.

10 Claims, No Drawings

ISOLATION OF HEPATITIS B e ANTIGEN

BACKGROUND OF THE INVENTION

It is known that the serum of numerous subjects who are carriers of Australia antigen ($HB_sAg$) contains another antigen which has been called hepatitis B e antigen ($HB_eAg$). See Magnius et al., *Acta. Path. Microbiol. Scand.*, Section B, 80, 335–337 (1972). Specimens of $HB_eAg$ are to be found at the Department of Virology, Statens Bakteriologeska Laboratorium, Stockholm and at the Liver Study Unit of Yale University, New Haven, Conn., U.S.A.

$HB_eAg$ is an antigenic complex of a group of soluble proteins (called $e_1$, $e_2$, etc.) which are normally found in acute hepatitis B cases as well as in the serum of chronic carrier cases of $HB_sAg$. $HB_eAg$ is also found in hemodialysed or in immunode-pressed subjects or in subjects suffering from Down's syndrome. These various antigen determinants are immunologically distinct from $HB_sAg$. It has been found that the administration of $HB_eAg$ elicits an immunological response with formation of hepatitis B e antibody ($HB_eAb$).

While $HB_eAg$ is present in biological fluid of individuals who have been infected with hepatitis B, the $HB_eAg$ frequently is present in concentration too low to be detected by present assays. As a result the fluid is considered negative for $HB_eAg$ and no attempt to recover e antigen therefrom is made.

It is also known that the biological fluid of healthy, chronic carriers of $HB_sAg$, in which the titers of $HB_sAg$ are relatively low, is positive for hepatitis B e antibody ($HB_eAb$). As presently available assays for this antibody are relatively insensitive, most of these fluids are considered negative for this antibody and recovery of the antibody is not attempted.

OBJECTS OF THE INVENTION

It is an object of the present invention to provide a method for separating and isolating $HB_eAg$ or $HB_eAb$ from human biological fluid. Another object is to provide a faster and more economical method for obtaining $HB_eAg$ or $HB_eAb$. These and other objects of the present invention will be apparent from the following description.

SUMMARY OF THE INVENTION

Human biological fluid containing $HB_eAg$ or $HB_eAb$ is subjected to banding in NaBr or two successive bandings in NaBr and sucrose and $HB_eAg$ or $HB_eAb$ is recovered in the density range of from about 1.04 to about 1.15 g/cc.

DETAILED DESCRIPTION

The starting material for the purified hepatitis B e antigen ($HB_eAg$) or hepatitis B e antibody ($HB_eAb$) of the present invention is human biological fluid containing hepatitis B surface antigen ($HB_sAg$). The presence of $HB_sAg$ in the human biological fluid serves as a marker for the presence of $HB_eAg$ or $HB_eAb$, even if assays yield a negative response for the presence of $HB_eAg$ or $HB_eAb$. The fluid may be any human biological fluid containing $HB_sAg$ such as, for example, plasma or menstrual blood. The most readily obtainable biological fluid is plasma. The plasma is obtained in conventional manner, e.g., by plasmaphoresis. The level of $HB_sAg$ in the human biological fluid may be measured in known manner by any suitable means, e.g., reversed passive hemagglutination or complement fixation. When the biological fluid is plasma, it is treated with $CaCl_2$ to allow the clotting of the fibrin, which is then removed by centrifugation. The converted plasma is then precipitated with ammonium sulfate to prepare a globulin rich fraction. The globulin precipitate is collected by centrifugation and then dissolved in saline and dialyzed against saline to remove most of the ammonium sulfate. The $HB_eAg$ or $HB_eAb$ in the human biological fluid is isolated by an isopycnic banding step and a rate zonal banding step.

In isopycnic banding the partially purified concentrate is contacted with a liquid medium having a density gradient therein which includes the density of the specific material being isolated. The liquid medium is then subjected to ultracentrifugation to attain an equilibrium distribution of the serum components through the density gradient, according to their individual densities. Successive fractions of the medium are displaced and those containing the desired antigen, i.e., the fractions having a density of from about 1.04 to about 1.15 g/cc, are separated.

The concentrations of the solutions forming the gradient are selected so as to encompass the density range of from about 1.0 to about 1.41 g/cc. The liquid medium may be employed in the form of a linear gradient or a step gradient. Preferably, it is employed in the form of a step gradient due to its inherent higher capacity for fractionation.

In rate zonal banding the 1.20–1.22 density range product from the isopycnic banding step is subjected to ultracentrifugation in contact with a liquid medium having a density gradient therein, but this time using the rate zonal technique, i.e., at a rate and for a period such that equilibrium is not attained, the $HB_eAg$ or $HB_eAb$ and other residual serum components being distributed through the medium according to their sedimentation coefficients in the medium. The concentrations of the solutions forming the step gradient are selected so as to encompass the density range of from about 1.0 to about 1.28 g/cc. The rate zonal step is carried out until the $HB_eAg$ or $HB_eAb$ resides in the 1.04 to 1.15 g/cc density region. At this point the $HB_eAg$ or $HB_eAb$ is separated from the bulk of the $HB_sAg$ and the high molecular weight macroglobulin components of the plasma.

The liquid media used in the isopycnic banding and rate zonal steps may be any density gradient in the appropriate ranges. Prior art solutes for such solutions include, e.g., sucrose, potassium bromide, cesium chloride, potassium tartrate and the like.

The isopycnic banding step is conveniently carried out in a centrifuge, for example, Electronucleonics-K, by filling the stationary rotor with saline solution, then successively displacing the saline solution upwards with aliquots of a liquid medium solution of increasing density until a step gradient is formed. The biological fluid is introduced at the top of the rotor displacing some of the highest density solution from the bottom. Typically, the volume of fluid is from about 15 to about 40% that of the step gradient. The centrifuge is brought up to speed through a programmed speed control system which prevents mixing during the initial reorientation phase. When equilibrium is attained and the product is in its proper density position, the rotor is slowed down through the same system to prevent mixing upon reorientation to the original configuration. Then the gradient is drained from below and the proper density cut collected. A similar technique is used in the rate zonal banding.

The 1.04–1.15 density range products from the isopycnic banding step (NaBr) and the rate zonal step (sucrose) are combined. The $HB_eAg$ or $HB_eAb$ product is dialyzed and concentrated, typically about a four-fold concentration. Amicon hollow fiber equipment is useful in the dialysis and concentration operations.

According to one aspect of the present invention the gradient is formed of sodium bromide whether or not the multiple loading technique is used. In contrast to heretofore used materials sodium bromide has definite advantages. The solubility of sodium bromide allows the use of high density solutions in the formation of gradients at refrigerator temperatures (2°–6° C.). There are definite economic advantages to using sodium bromide over a salt such as cesium chloride as well as not having to contend with the problem of human toxicity from residual and $HB_sAg$ bound cesium ions. In sodium bromide gradient any ions bound to the $HB_eAg$ due to biophysical characteristics, will be a sodium salt which is very compatible with the human biological system and does not present a toxicity problem.

The superior solubility of NaBr at lowered temperatures with respect to KBr permits the use of lowered temperatures more conductive to stability of biological materials. The use of a step gradient rather than a linear gradient is preferred as it accumulates impurities at the step boundaries and permits processing a larger volume of plasma in a single gradient.

The following examples illustrate the present invention without, however, limiting the same thereto.

EXAMPLE 1

20 Liters of plasma having an $HB_sAg$ titer as measured by complement fixation $\geq 256$ is mixed with 2.2 liters of 2.77% $CaCl_2$ and transferred to large centrifuge bottles. After 2 hours at 37° C. ($H_2O$ bath) the clotted plasma is centrifuged to clear the converted serum. The supernatant fluid is mixed with an equal volume of ammonium sulfate solution (450 mgs/ml) and stored at 5° C. overnight. The precipitate which forms is collected by batch centrifugation at 7000 X g for 30 minutes using the JA-10 rotor (3 liter capacity per batch). The pellets post centrifugation are suspended in about 2.25 liters of saline. The concentrated suspension is then dialyzed against 40 liters of saline to remove the ammonium sulfate.

The rotor of a centrifuge, Electronucleonics K, is filled with 8,400 ml of phosphate buffer. After running the rotor up to 10,000 rpm to degas the system, the following step gradient is pumped into the bottom of the stationary rotor:
1. 2,000 ml of 10% NaBr, d=1.08
2. 1,000 ml of 20% NaBr, d=1.17
3. 1,500 ml of 30% NaBr, d=1.28
4. 3,900 ml of 40% NaBr, d=1.41

The dialyzed suspension, 2,250 ml, is pumped into the top of the stationary rotor displacing 2,250 ml of 40% NaBr from the bottom of the rotor. The rotor is accelerated to 30,000 rpm and run at this speed for 18 hours. After stopping the rotor 1,000 ml of $HB_eAg$ rich material in the 1.05–1.15 g/cc density region is collected.

A second collection (3,000 ml) is made of material in the higher density range of from 1.17 to 1.22 g/cc. This material which is rich in $HB_sAg$ is dialyzed against phosphate buffered saline (PBS) and concentrated to 1,000 ml. Amicon hollow fiber equipment is used in this operation.

The rotor is then filled with phosphate buffer, degassed as above, and the following step gradient pumped into the bottom of the stationary rotor:
1. 2,000 ml of 5% sucrose, d=1.02
2. 1,650 ml of 15% sucrose, d=1.06
3. 1,750 ml of 25% sucrose, d=1.10
4. 4,300 ml of 50% sucrose, d=1.23

The second higher density range material from the NaBr isopycnic banding step, 1,000 ml, is pumped into the rotor top displacing 1,000 ml of 50% sucrose out the rotor bottom. The rotor is then run at 28,000 rpm for 18 hours. After stopping the rotor, 1,000 ml of $HB_eAg$ rich material in the 1.05–1.15 g/cc density region is collected.

The 1.05–1.15 density range products from the isopycnic banding step (NaBr) and the rate zonal step (sucrose) are combined (~2 liters). The $HB_eAg$ product is dialyzed against PBS and concentrated four fold to 500 ml. Amicon hollow fiber equipment is used in the dialysis and concentration operations.

EXAMPLE 2

20 Liters of plasma having an $HB_sAg$ titer as measured by complement fixation $\leq 128$ are mixed with 2.2 liters of 2.77% $CaCl_2$ and transferred to large centrifuge bottles. After 2 hours at 37° C. ($H_2O$ bath) the clotted plasma is centrifuged to clear the converted serum. The supernatant fluid is mixed with an equal volume of ammonium sulfate solution (450 mgs/ml) and stored at 5° C. overnight. The precipitate which forms is collected by batch centrifugation at 7000 X g for 30 minutes using the JA-10 rotor (3 liter capacity per batch). The pellets post centrifugation are suspended in about 2.25 liters of saline. The concentrated suspension is then dialyzed against 40 liters of saline to remove the ammonium sulfate.

The rotor of a centrifuge, Electronucleonics K, is filled with 8,400 ml of phosphate buffer. After running the rotor up to 10,000 rpm to degas the system, the following step gradient is pumped into the bottom of the stationary rotor:
1. 2,000 ml of 10% NaBr, d=1.08
2. 1,000 ml of 20% NaBr, d=1.17
3. 1,500 ml of 30% Nabr, d=1.28
4. 3,900 ml of 40% NaBr, d=1.41

The dialyzed suspension, 2,250 ml, is pumped into the top of the stationary rotor displacing 2,250 ml of 40% NaBr from the bottom of the rotor. The rotor is accelerated to 30,000 rpm and run at this speed for 18 hours. After stopping the rotor 1,500 ml of $HB_eAb$ rich material in the 1.04–1.15 g/cc density region is collected.

A second collection (3,000 ml) is made of material in the higher density range of from 1.17 to 1.22 g/cc. This material which is rich in $HB_sAg$ is dialyzed against phosphate buffered saline (PBS) and concentrated to 1,000 ml. Amicon hollow fiber equipment is used in this operation.

The rotor is then filled with phosphate buffer, degassed as above, and the following step gradient pumped into the bottom of the stationary rotor:
1. 2,000 ml of 5% sucrose, d=1.02
2. 1,650 ml of 15% sucrose, d=1.06
3. 1,750 ml of 25% sucrose, d=1.10
4. 4,300 ml of 50% sucrose, d=1.23

The second higher density range material from the NaBr isopycnic banding step, 1,000 ml, is pumped into the rotor top displacing 1,000 ml of 50% sucrose out the rotor bottom. The rotor is then run at 28,000 rpm for 18 hours. After stopping the rotor, 1,500 ml of HB$_e$Ab rich material in the 1.04–1.15 g/cc density region is collected.

The 1.04–1.15 density range products from the isopycnic banding step (NaBr) and the rate zonal step (sucrose) are combined (~3 liters). The HB$_e$Ab product is dialyzed against PBS and concentrated six fold to 500 ml. Amicon hollow fiber equipment is used in the dialysis and concentration operations.

EXAMPLE 3

An immunodiffusion assay is performed using 0.8% Agarose Rheophoresis plates (Abbott Labs). The plastic ring is carefully removed from the plate and the trough is filled with Tris buffer to check that the agar is intact. The six outside wells are each filled with 50 μl of plasma to be tested for presence of HB$_e$Ab. A portion of the HB$_e$Ag rich material from the NaBr (isopycnic) banding step of Example 1 is dialyzed against PBS and concentrated four fold. The center well is filled with 20 μl of the concentrated material. The rheophoresis plate is incubated at room temperature in a humidified plastic box. The results are recorded after seven days of incubation. The presence of a precipitate confirms the presence of HB$_e$Ab in the plasma. The plate is photographed as a final record of the results.

EXAMPLE 4

An immunodiffusion assay is performed using 0.8% Agarose Rheophoresis plates (Abbott Labs). The plastic ring is carefully removed from the plate and the trough is filled with Tris buffer to check that the agar is intact. The six outside wells are each filled with 50 μl of plasma to be tested for presence of HB$_e$Ag. A portion of the HB$_e$Ab rich material from the NaBr (isopycnic) banding step of Example 2 is dialyzed against PBS and concentrated five fold. The center well is filled with 20 μl of the concentrated material. The rheophoresis plate is incubated at room temperature in a humidified plastic box. The results are recorded after seven days of incubation. The presence of a precipitate confirms the presence of $HB_eAg$ in the plasma. The plate is photographed as a final record of the results.

EXAMPLE 5

The procedure of Example 4 is repeated except substituting the $HB_eAg$ rich material from the sucrose (rate zonal) banding step for the $HB_eAg$ rich material from the NaBr (isopycnic) banding step. The presence of a precipitate confirms the presence of $HB_eAg$ in the plasma.

EXAMPLE 6

The procedure of Example 3 is repeated except that the center well is filled with 20 μl of the combined $HB_eAg$ product from the final step of Example 1. The presence of a precipitate confirms the presence of $HB_eAb$ in the plasma.

EXAMPLE 7

The procedure of Example 4 is repeated except that the center well is filled with 20 μl of the combined $HB_eAb$ product from the final step of Example 2. The presence of a precipitate confirms the presence of $HB_eAg$ in the plasma.

What is claimed is:

1. A method for isolating hepatitis B e antigen or hepatitis B e antibody which comprises isopycnically banding human biological fluid which contains hepatitis B surface antigen, recovering a fraction having a density range of from about 1.04 to about 1.15 g/cc, and and isolating $HB_eAb$ if the plasma has an $HB_sAg$ titer measured by complement fixation of at least about 256, or isolating $HB_eAg$ if the plasma has an $HB_sAg$ titer measured by complement fixation of less than about 128.

2. A method according to claim 1 wherein the human biological fluid is clarified plasma.

3. A method according to claim 1 wherein the isopycnic banding is effected in an aqueous solution of NaBr.

4. A method for isolating hepatitis B e antigen which comprises isopycnically banding human biological fluid which has a hepatitis B surface antigen titer measured by complement fixation of at least about 256, recovering a first fraction having a density range of from about 1.04 to about 1.15 g/cc, recovering a second fraction in the density range of from about 1.17 to about 1.22 g/cc, dialyzing and concentrating the second fraction, subjecting the concentrated second fraction to rate zonal banding and recovering a third fraction having a density range of from about 1.04 to about 1.15 g/cc, and dialyzing and concentrating the first and third fractions.

5. A method according to claim 4 wherein the human biological fluid is clarified plasma.

6. A method for isolating hepatitis B e antibody which comprises isopycnically banding human biological fluid which has a hepatitis B surface antigen titer as measured by complement fixation of less than about 128, recovering a first fraction having a density range of from about 1.04 to about 1.15 g/cc, recovering a second fraction in the density range of from about 1.17 to about 1.22 g/cc, dialyzing and concentrating the second fraction, subjecting the concentrated second fraction to rate zonal banding and recovering a third fraction having a density range of from about 1.04 to about 1.04 to about 1.15 g/cc, and dialyzing and concentrating the first and third fractions.

7. A method according to claim 6 wherein the human biological fluid is clarified plasma.

8. A method according to claim 3 wherein the aqueous solution is a density gradient.

9. A method according to claim 4 wherein the isopycnic banding is effected in an aqueous solution of NaBr.

10. A method according to claim 6 wherein the isopycnic banding is effected in an aqueous solution of NaBr.

* * * * *

UNITED STATES PATENT AND TRADEMARK OFFICE
CERTIFICATE OF CORRECTION

PATENT NO. : 4,204,989
DATED : May 27, 1980
INVENTOR(S) : McAleer et al.

It is certified that error appears in the above—identified patent and that said Letters Patent is hereby corrected as shown below:

Claim 1, line 6, change "HBeAb" to --HBeAg--.

Claim 1, line 8, change "HBeAg" to --HBeAb--.

Signed and Sealed this

Fifth Day of October 1982

[SEAL]

Attest:

GERALD J. MOSSINGHOFF

Attesting Officer       Commissioner of Patents and Trademarks